United States Patent [19]
Böger et al.

[11] Patent Number: 5,939,424
[45] Date of Patent: Aug. 17, 1999

[54] COMPOUNDS FOR TREATING DISORDERS OF LIPID METABOLISM AND THEIR PREPARATION

[75] Inventors: Hans Georg Böger, Waldems Esch; Axel Hoffmann, Frankfurt; Gerhard Jähne, Frankfurt; Norbert Krass, Frankfurt; Hans-Ludwig Schäfer, Mainz-Kastel, all of Germany

[73] Assignee: Hoechst Aktiengesellschaft, Frankfurt am Main, Germany

[ * ] Notice: This patent is subject to a terminal disclaimer.

[21] Appl. No.: 08/868,991

[22] Filed: Jun. 4, 1997

[30] Foreign Application Priority Data

Jun. 24, 1996 [DE] Germany .............................. 196 25 089

[51] Int. Cl.⁶ ........................ A61K 31/505; C07D 403/04
[52] U.S. Cl. ............................ 514/275; 544/324; 544/325
[58] Field of Search ..................................... 544/325, 324; 514/275

[56] References Cited

U.S. PATENT DOCUMENTS 5,571,816   11/1996   Kampe et al. .......................... 514/275

FOREIGN PATENT DOCUMENTS

| 0 206 297 | 12/1986 | European Pat. Off. . |
| 0 557 879 | 9/1993 | European Pat. Off. . |
| 0 577 877 | 9/1993 | European Pat. Off. . |
| 28 53 220 | 7/1980 | Germany . |

OTHER PUBLICATIONS

Chomczynski et al., "Single–Step Method of RNA Isolation by Acid Guanidinium Thiocyanate–Phenol–Chloroform Extraction," Analytical Biochemistry, vol. 162, pp. 156–159, 1987.

Primary Examiner—Richard L. Raymond
Assistant Examiner—Ann M. Kessinger
Attorney, Agent, or Firm—Foley & Lardner

[57] ABSTRACT

The invention relates to 4-Amino-2-ureidopyrimidine-5-carboxamides of the formula I

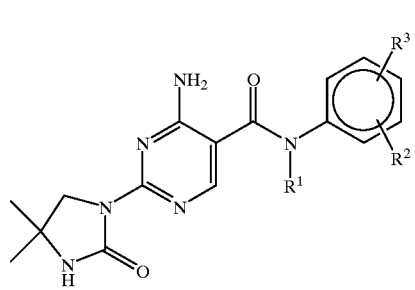

in which $R^1$ is H or $(C_1-C_8)$-alkyl, where one or more H can be replaced by F; $R^2$ is selected from the group consisting of F, Cl, Br, H, -O-$(C_1-C_8)$-alkyl, and -S-$(C_1-C_8)$-alkyl, where the alkyl groups have one or more H replaced by F; $R^3$ is -O-$(C_1-C_8)$-alkyl or -S-$(C_1-C_8)$-alkyl, where the alkyl groups have one or more H replaced by F; or $R^2$ and $R^3$ together form -O-$(C_1-C_5)$-alkylene-O-, where the alkylene portion has one or more H replaced by F; and their physiologically tolerable salts. The invention further provides processes for preparing the compounds of formula I. The compounds are suitable for the treatment of disorders of lipid metabolism.

13 Claims, No Drawings

COMPOUNDS FOR TREATING DISORDERS OF LIPID METABOLISM AND THEIR PREPARATION

BACKGROUND OF THE INVENTION

The invention relates to tertiary amides of 4-amino-2-ureidopyrimidine-5-carboxylic acid and their acid addition salts. In particular, the invention relates to substituted 4-amino-2(imidazolidin-2-on-1-yl)pyrimidine-5-N-(fluoroalkyl)-N-(substituted)phenylcarboxamides and their acid addition salts.

The use of 4-amino-2-ureidopyrimidine-5-N-(alkyl-N-phenyl)carboxamides to treat adiposity and disorders of lipid metabolism has been described [cf. European Patent 0 557 879]. However, the tolerability of the 4-amino-2-ureidopyrimidine-5-carboxamides proposed as pharmaceuticals in European Patent 0 557 879 is not entirely satisfactory. Thus, these substances show cytotoxic effects at higher doses, and such side effects are undesirable in therapeutic uses. Therefore, there exists in the art an unmet need for non-toxic compounds that are useful in treating adiposity and disorders of lipid metabolism.

SUMMARY OF THE INVENTION

Accordingly, one object of the present invention is to provide compounds which display a therapeutically utilizable hypolipidemic effect combined with good tolerability. In this connection, a particular object was to find compounds with adequate hypolipidemic action, but with reduced or eliminated cytotoxic properties as compared to the compounds described in European Patent 0 557 879.

A further object of the invention resides in providing a process for preparing the compounds according to the invention.

Still another object of the invention resides in the provision of pharmaceutical preparations and methods of treating disorders of lipid metabolism using the compounds according to the invention.

Therefore, according to one aspect, the invention provides 4-amino-2-ureidopyrimidine-5-carboxamide compounds of formula I,

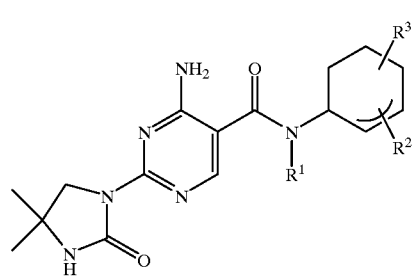

in which $R^1$ is hydrogen or a $(C_1-C_8)$-alkyl, in which one or more or all hydrogens can be replaced by fluorine, $R^2$ is selected from the group consisting of fluorine, chlorine, bromine, hydrogen, -O-$(C_1-C_8)$-alkyl, and -S-$(C_1-C_8)$-alkyl, where the alkyl radicals have one or more or all hydrogens replaced by fluorine, $R^3$ is -O-$(C_1-C_8)$-alkyl or -S-$(C_1-C_8)$-alkyl, where the alkyl radicals have one or more or all hydrogens replaced by fluorine, or $R^2$ and $R^3$ together can form a radical of the formula -O-$(C_1-C_5)$-alkylene-O-, where the alkylene portion has one or more or all hydrogens replaced by fluorine, or its physiologically tolerable acid addition salts.

According to another aspect, the invention provides a process for preparing the compounds of formula I comprising the following reaction scheme:

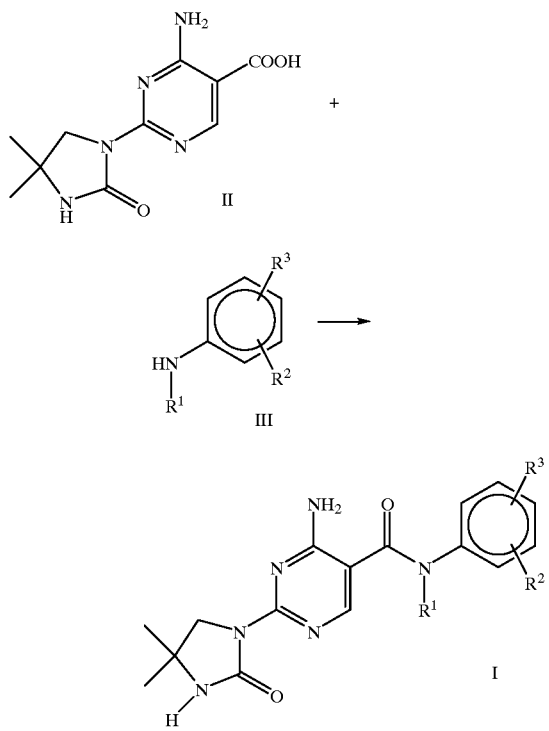

which involves converting a compound of the formula II into the corresponding acid chloride and reacting said acid chloride with a compound of formula III, in which $R^1$, $R^2$ and $R^3$ are as defined above, at a temperature from 0° C. to 200° C. in a suitable solvent, with or without addition of an auxiliary base, to give a compound of formula I, and optionally converting said compound of formula I into a physiologically tolerable salt or converting a salt obtained into a physiologically tolerable salt.

A further aspect of the invention provides a second process for preparing the compounds of formula I comprising the following reaction scheme:

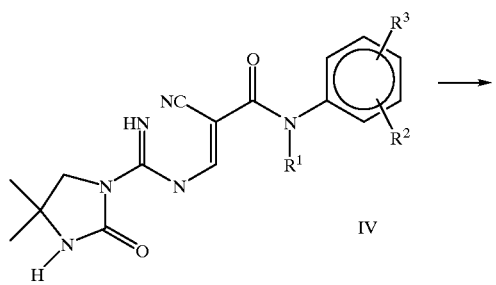

-continued which involves cyclizing a compound of formula IV, in which $R^1$, $R^2$ and $R^3$ are as defined above, to a compound of formula I.

Yet another aspect of the invention provides pharmaceutical preparations of the compounds of formula I and methods of treating disorders of lipid metabolism using the compounds of formula I.

Further objects, features and advantages of the present invention will become apparent from the detailed description of preferred embodiments that follows.

DESCRIPTION OF THE PREFERRED EMBODIMENTS

The invention relates to 4-Amino-2-ureidopyrimidine-5-carboxamides, processes for their preparation, pharmaceuticals comprising these compounds, and methods for their use.

COMPOUNDS OF THE INVENTION

The inventive 4-amino-2-ureidopyrimidine-5-carboxamide compounds are described with reference to formula I:

I in which $R^1$ is hydrogen or a $(C_1–C_8)$-alkyl, in which one or more or all hydrogens can be replaced by fluorine, $R^2$ is selected from the group consisting of fluorine, chlorine, bromine, hydrogen, -O-$(C_1–C_8)$-alkyl, and -S-$(C_1–C_8)$-alkyl, where the alkyl radicals have one or more or all hydrogens replaced by fluorine, $R^3$ is -O-$(C_1–C_8)$-alkyl or -S-$(C_1–C_8)$-alkyl, where the alkyl radicals have one or more or all hydrogens replaced by fluorine, or $R^2$ and $R^3$ together can form a radical of the formula -O-$(C_1–C_5)$-alkylene-O-, where the alkylene portion has one or more or all hydrogens replaced by fluorine, and their physiologically tolerable acid addition salts.

Preferred compounds of formula I are those in which one or more radical(s) has or have the following meaning:

$R^1$ is $(C_1–C_4)$-alkyl, in which one or more or all hydrogens can be replaced by fluorine, $R^2$ is selected from the group consisting of fluorine, chlorine, bromine, hydrogen, -O-$(C_1–C_4)$-alkyl, and -S-$(C_1–C_4)$-alkyl, where the alkyl radicals have one or more or all hydrogens replaced by fluorine, $R^3$ is -O-$(C_1–C_4)$-alkyl or -S-$(C_1–C_4)$-alkyl, where the alkyl radicals have one or more or all hydrogens replaced by fluorine, or $R^2$ and $R^3$ together can form a radical of the formula -O-$(C_1–C_5)$-alkylene-O-, where the alkylene portion has one or more or all hydrogens replaced by fluorine, and their physiologically tolerable acid addition salts.

Particularly preferred compounds of the formula I are those in which one or more radical(s) has or have the following meaning:

$R^1$ is $(C_1–C_4)$-alkyl, in which one or more or all hydrogens can be replaced by fluorine, $R^2$ is hydrogen or bromine, $R^3$ is —$OCF_3$, and their physiologically tolerable acid addition salts.

Specific preferred compounds include 4-Amino-2-(4,4-dimethylimidazolidin-2-on-1-yl)-5-[N-methyl-N-(2-trifluoromethoxy)phenyl]pyrimidinecarboxamide hydrochloride, 4-Amino2-(4,4-dimethylimidazolidin-2-on-1-yl)-5-(3-trifluoromethoxyphenylpyrimidine)carboxamide, 4-Amino-2-(4,4-dimethyl-2-oxo-1-imidazolidin-2-on-1-yl)-5-[Nethyl-N-(3-trifluoromethoxy)phenyl] pyrimidinecarboxamide hydrochloride, 4-Amino-2(4,4-dimethylimidazolidin-2-on-1-yl)-5-[N-(2,2,2-trifluoroethyl)-N(3-trifluoromethoxyphenyl)] pyrimidinecarboxamide, 4-Amino-2-(4,4-dimethylimidazolidin-2on-1-yl)- 5-[N-(2,2,3,3,3-pentafluoropropyl)-N-(3-trifluoromethoxy)phenyl] pyrimidinecarboxamide hydrochloride, 4-Amino-2-(4,4-dimethylimidazolidin-2-on-1-yl)-5-[N-(3-(2,2,3,3-tetrafluoroethoxy)phenyl)]pyrimidinecarboxamide hydrochloride, 4-Amino-2-(4,4-dimethylimidazolidin-2-on-1-yl)-5-[N-methyl-N-(3-(2,2,3,3-tetrafluoroethoxy)phenyl)] pyrimidinecarboxamide hydrochloride, 4-Amino-2-(4,4-dimethylimidazolidin-2-on-1-yl)-5-[N-methyl-N-(4-trifluoromethoxyphenyl)]pyrimidinecarboxamide hydrochloride, 4-Amino-2-(4,4-dimethyl-2-imidazolidin-2-on-1-yl)-5-[N-(2-trifluoromethoxyphenyl)] pyrimidinecarboxamide hydrochloride, 4-Amino-2-(4,4-dimethylimidazolidin-2-on-1-yl)-5-[N-(4-trifluoromethoxyphenyl)]pyrimidinecarboxamide hydrochloride, 4-Amino-2-(4,4-dimethylimidazolidin-2on-1-yl)-5-[N-3-(difluoromethylthio)phenyl] pyrimidinecarboxamide hydrochloride, 4Amino-2-(4,4-dimethylimidazolidin-2-on-1-yl-5-[N-methyl-(3-trifluoromethoxyphenyl)]pyrimidinecarboxamide, 4-Amino-2-(4,4-dimethylimidazolidin-2-on-1-yl)5-[N-(3-difluoromethoxyphenyl)]pyrimidinecarboxamide hydrochloride, 4-Amino-2-(4,4dimethylimidazolidin-2-on-1-yl)-5-[N-(2,2-difluorobenzo-1,3-dioxol-5-yl)] pyrimidinecarboxamide hydrochloride, 4-Amino-2-(4,4-dimethylimidazolidin-2-on-1yl)-5-[N-(2,2,3,3-tetrafluorobenzo-1,4-dioxan-6-yl)]pyrimidinecarboxamide hydrochloride, 4-Amino-2-(4,4-dimethylimidazolidin-2-on-1-yl)-5-[N-(3-chloro4-trifluoromethoxyphenyl)] pyrimidinecarboxamide hydrochloride, 4-Amino-2-(4,4dimethylimidazolidin-2-on-1-yl)-5-[N-(3-bromo-4-trifluoromethoxyphenyl)]pyrimidinecarboxamide hydrochloride, 4-Amino-2-(4,4dimethylimidazolidin-2-on-1-yl)-5-[N-3-(2,2,2-trifluoroethoxy)phenyl] pyrimidinecarboxamide hydrochloride, 4-Amino-2-(4,4dimethylimidazolidin-2-on-1-yl)-5-[N4-(2,2,2- trifluoroethoxy)phenyl]pyrimidinecarboxamide hydrochloride, 4-Amino-2-(4,4dimethylimidazolidin-2-on-1-yl)-5-[N-(3-pentafluoroethoxy)phenyl]pyrimidinecarboxamide, 4-Amino-2-(4,4-dimethylimidazolidin-2-on-1-yl)-N-(6-fluoro-3-trifluoromethoxyphenyl)pyrimidinecarboxamide, 4-Amino-2-(4,4-dimethylimidazolidin-2-on-1-yl)-5-[N-(3-trifluorothiomethylphenyl)]pyrimidinecarboxamide hydrochloride and physiologically tolerable acid addition salts thereof.

Physiologically tolerable acid addition salts are understood as meaning compounds which are easily soluble, soluble or sparingly soluble in water according to the definition in the "Deutsches Arzneibuch" [German Pharmacopeia] (9th Edition 1986, Official Issue, Deutscher Apotheker-Veriag Stuttgart), page 19. The hydrochlorides and sulfates of the compounds are preferred.

PROCESSES OF THE INVENTION

The invention furthermore relates to two processes for the preparation of 4-amido-2-ureidopyrimidine-5-carboxamides of the formula I. These processes are set forth below as Process A and Process B.

Process A:

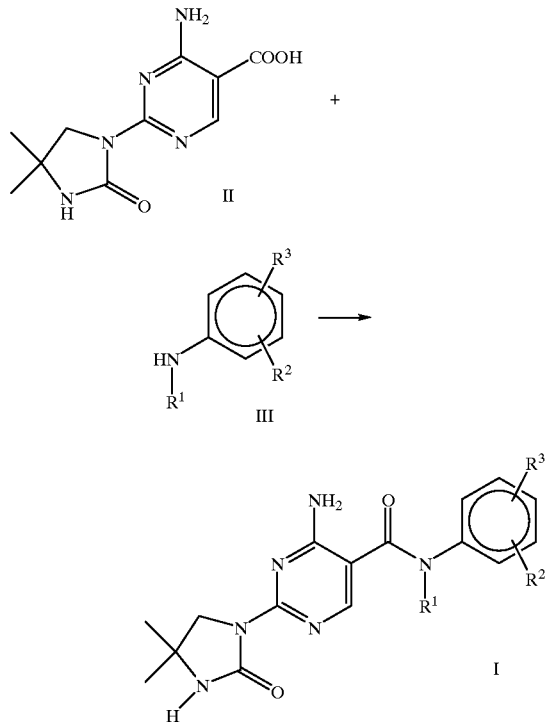

Process A for the preparation of the compounds of formula I comprises reacting a compound of the formula II after an in situ activation (conversion into the corresponding acid chloride, for example, using thionyl chloride), with a compound of formula III, in which $R^1$, $R^2$ and $R^3$ have the meaning indicated for formula I, at a temperature from 0° C. to 200° C. in a suitable solvent (such as, for example, DME) with or without addition of an auxiliary base (such as, for example, $NEt_3$) to give a compound of the formula I, and optionally converting the obtained compound of the formula I into a physiologically tolerable salt or optionally converting a salt which is obtained into a physiologically tolerable salt.

Process B:

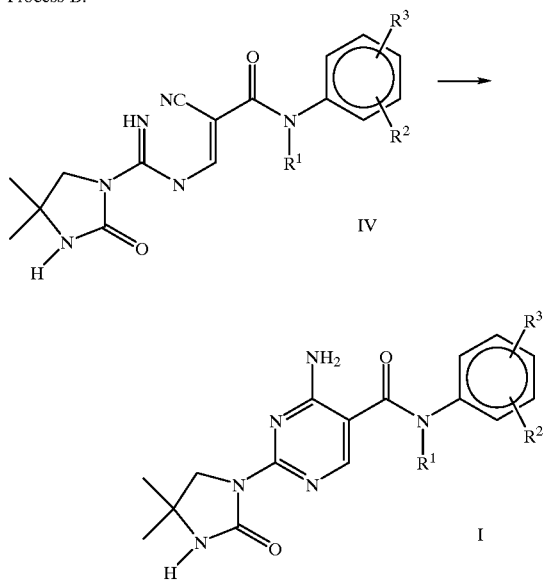

Process B for the preparation of the compounds of the formula I comprises cyclizing a compound of the formula IV, in which $R^1$, $R^2$ and $R^3$ have the meanings indicated for formula I, to a compound of formula I. The preparation of the compounds of type IV, and 1 5 also the cyclization to give compounds of type 1, are described in EP-0 557 879.

Starting Material for Process A

The 4-amino-2-(4,4-dimethylimidazolidin-2-on-1-yl)pyrimidine-5-carboxylic acids, whose acid chloride forms the starting material of process A, is prepared as follows:

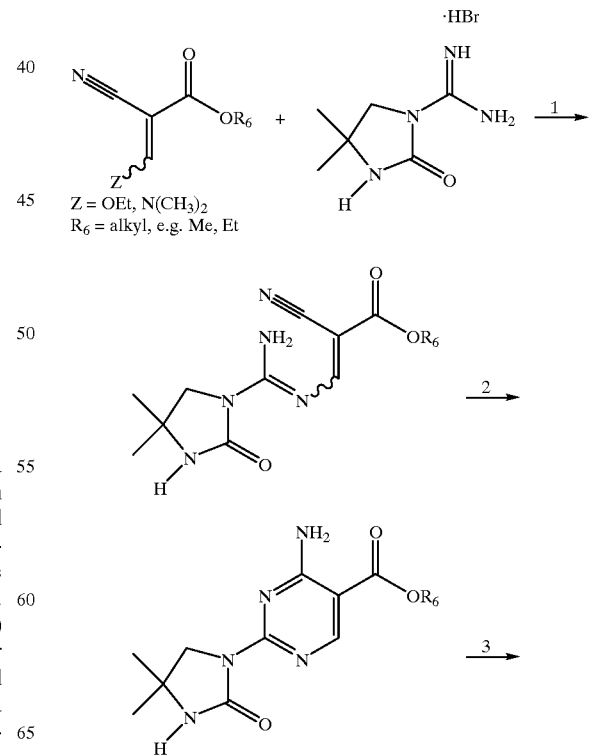

Z = OEt, N(CH$_3$)$_2$
R$_6$ = alkyl, e.g. Me, Et

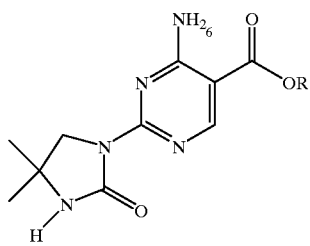

In the first stage, 1-amidino4,4-dimethylimidazolidin-2-one hydrobromide and alkyl 2-cyano-3-alkoxyacrylate, or alkyl 2-cyano-3-dimethylaminoacrylate, are reacted at a temperature from 0° to 150° C. in a suitable solvent, such as, for example, isopropanol, in 5 the presence of base, such as, for example, KOH, to give alkyl 3-(1-amidino4, 4dimethylimidazolidin-2-one)-2-cyanoacrylate.

In the second stage, alkyl 3-(1-amidino4,4-dimethylimidazolidin-2-one)-2-cyanoacrylate is cyclized at a temperature from 0° to 150° C. in a suitable solvent, such as, for example, toluene, in the presence of trifluoroacetic acid or acetic acid to give alkyl 4-amino-2-(4, 4dimethylimidazolidin-2-on-1-yl)pyrimidine-5-carboxylate.

In the third stage, the alkyl 4-amino-2-(4,4-dimethylimidazolidin-2-on-1-yl)pyrimidine-5carboxylate is hydrolyzed according to known methods to give 4-amino-2-(4,4-dimethylimidazolidin-2-on-1-yl)pyrimidine-5-carboxylic acid.

Pharmaceutical Preparations

The present invention also relates to pharmaceutical preparations which, in addition to nontoxic, inert pharmaceutically suitable excipients, contain one or more active compounds according to the invention or which consist of one or more active compounds according to the invention. The pharmaceutical preparations of the invention can also contain further pharmaceutically active compounds in addition to the active compounds according to the invention. The invention further relates to processes for the production of these pharmaceutical preparations.

Nontoxic inert pharmaceutically suitable excipients are understood as meaning pharmaceutically acceptable solid, semisolid or liquid diluents, fillers and formulation auxiliaries of any type, which after mixing with the active compound bring this into a form suitable for administration. Suitable administration forms of the compounds according to the invention are, for example, tablets, coated tablets, capsules, pills, aqueous solutions, suspensions and emulsions, if appropriate sterile injectable solutions, non-aqueous emulsions, suspensions and solutions, sprays and also preparation forms with protracted release of active compound(s).

The therapeutically active compounds should be present in the above-mentioned pharmaceutical preparations expediently in a concentration of approximately 0.1 to 99, preferably of 0.5 to 70, percent by weight of the total mixture. The administration concentrations for solutions and aerosols in the form of spray is in general 0.1 to 20, preferably 0.5–5, percent by weight. The active compounds or the pharmaceutical preparations of the invention can be administered orally, parenterally, intraperitoneally and/or rectally.

The above-mentioned pharmaceutical preparations are prepared in a customary manner according to known methods, e.g. by mixing the active compound(s) with the excipient(s).

The compounds of the present invention and their salts which are utilizable, for example, as hypolipidemics can be used for the production of pharmaceutical preparations which contain an effective amount of the active substance together with excipients and which are suitable for enteral and parenteral administration. Tablets or capsules (gelatin capsules) are preferably used which contain the active compound together with diluents or excipients, e.g. lactose, dextrose, cane sugar, mannitol, sorbitol, cellulose, various types of starch and/or glycerol, and lubricants such as silica, talc, stearic acid or its salts, such as magnesium or calcium stearate, and/or polyethylene glycol. Tablets can also contain binders such as magnesium carbonate, magnesium aluminum silicate, starch, gelatin, tragacanth, methylcellulose, sodium carboxymethylcellulose and/or polyvinylpyrrolidone and, if required, colorants, flavorings and sweeteners. Injectable solutions are preferably isotonic aqueous solutions or suspensions, which can be sterilized and can contain auxiliaries, such as preservatives, stabilizers, wetting agents and/or emulsifiers, solubilizers, salts for regulating the osmotic pressure and/or buffer substances. The pharmaceutical preparations according to the invention, which if desired can contain further pharmacologically active substances, are prepared, for example, by means of conventional mixing, granulating and pan-coating processes, and contain 0.1% to preferably 80%, preferably approximately 5% to approximately 65%, of the active compound.

Oral administration takes place in pharmaceutically customary preparations, for example, in the form of tablets, coated tablets or capsules, which, for example, per daily dose contain 5 to 1000 mg, preferably 20 to 200 mg, of the active compound as a mixture with a customary excipient and/or constituent, it being possible to give individual doses of 5 to 200 mg, preferably once to three times daily.

It may, however, be necessary to deviate from the doses mentioned, namely depending on the nature and the body weight of the subject to be treated, the nature and severity of the disease, the type of preparation and of administration of the pharmaceutical, and the time or interval within which administration takes place. Thus in some cases it may be adequate to manage with less than the above-mentioned amount of active compound, while in other cases the above-mentioned amount of active compound has to be exceeded. The setting of the optimum dose and type of administration of the active compounds necessary in each case can easily be carried out by persons skilled in the art on the basis of their expert knowledge.

Clinical Applications

Due to their low cytotoxicity, the compounds of formula I and their physiologically tolerable salts are ideal pharmaceuticals for the treatment of disorders of lipid metabolism, especially hyperlipidemia. By stimulating the LDL receptor, the compounds are particularly suitable for effectively lowering the plasma lipid levels. Accordingly, a therapeutically effective amount of an invnetive compound, or composition thereof, can include an amount of the compound that stiumulates production of LDL receptors or lowers plasma lipid levels as measured by convnetional techniques. The following results confirm the pharmacological activity and low toxicity of the inventive compounds.

The Inventive Compounds Increase LDL Receptor mRNA Levels

To test the ability of the inventive compounds to lower plasma lipid levels, the stimulation of LDL receptor mRNA production was chosen as a surrogate. Thus, in rat livers, within a few hours the LDL receptor mRNA levels are increased by the compounds of the formula I (Table I). The stimulation is in the range from 170 to 350% of the controls (control=100%). Accordingly, this surrogate system clearly demonstrates the pharmacological activity of the compounds of the invention.

The preparation of the mRNA was carried out according to the method of Chomczynski, P. and Sacchi, N., Anal. Biochem. 162, 156–159 (1987). In organs (such as, for example, liver), the deep-frozen tissue was homogenized on dry ice beforehand in a mortar and the mRNA was further enriched by means of Oligo dT according to standard methods (cf. Sambrook, J., Fritsch, E. F. and Maniatis, T., Molecular Cloning, second Edition, Cold Spring Harbor (1989); in this collection of methods, there are also descriptions of all further relevant molecular biology standard methods used here). Five to 20 mm of the dissolved mRNA thus obtained were denatured according to standard methods and separated on 1% horizontal agarose gels. The mRNA was transferred to Hybond N membranes (Amersham) by means of capillary blot. The specific hybridization probe used was a partial LDL receptor cDNA clone and the internal standard a plasmid which contained a β-actin gene. Both plasmids were labeled by means of a random primer kit from Amersham up to a specific activity of $5 \times 10^9$ cpm/mg. Prehybridization, hybridization and washing of the filters were carried out by standard methods. The filters were then exposed at −70° C. on Cronex 4 films (Dupont) overnight up to 14 days in the presence of an intensifying screen and the hybridization signals were quantified using a commercial laser densitometer by means of the film-blackening intensity. The quotient of the intensity of the LDL receptor band and of the actin band was then determined as an internal standard to correct yield variations.

TABLE I

| Compounds according to Example | Concentration | LDL receptor mRNA |
|---|---|---|
| 2 | 30 mg/kg | 250% |
| 3 | 30 mg/kg | 235% |
| 4 | 30 mg/kg | 230% |
| 14 | 30 mg/kg | 250% |
| 15 | 30 mg/kg | 242% |
| 22 | 30 mg/kg | 235% |

Table I shows the stimulation of the LDL receptor mRNA expression in rat livers 6 hours after administration of selected compounds of formula I (dose of 30 mg/kg). Liver tissue was removed and shock-frozen in liquid nitrogen. The mRNA was then isolated as described, and the relative LDL receptor mRNA levels were determined by means of the Northern blot technique. The mRNA levels of untreated control animals were set at 100%, and the stimulation of the LDL receptor mRNA in percent of the control was calculated.

The Inventive Compounds Have Reduced Cytotoxicity

As a measure of cytotoxicity, the effects of representative inventive compounds on the proliferation of three different cell lines was determined. These data, presented below in Table II, demonstrate that the instant compounds have significantly reduced cytotoxic effects as compared to a representative compound of EP 0 557 879.

Exponentially growing tumor cells (e.g., bronchial carcinoma cells, A549, colon carcinoma cells, HT29, renal carcinoma cells, Hela cells) are inoculated into 96 hole microtiter plates in a concentration of $5 \times 10^3$ cells per ml in RPMI standard medium.

Incubation with test substance concentration series takes place for 72 hours at 37° C., 5% $CO_2$, 95% rel. atmospheric humidity. Each compound concentration or control is tested here in four parallel incubations. After 65 hours, 50 ml of MUT [3-(4,5-dimethyl2-thiazolyl)-2,5-diphenyl-2 H-tetrazolium bromide] in 2.5 mg/ml of PBS are added. In 1 5 intact cells, MTT is reduced to a red insoluble dye. Depending on the cell line used, the supernatant is removed after a further 7 to 24 hours incubation. The resulting insoluble dye is dissolved in 100 ml of DMSO with careful shaking, and the extinction is measured at 492 nm in a 340 CC multiscan photometer from Flow.

The results are calculated as quotients from the meaned extinction values of the test substances and of the control values. The variations in the individual determination values within the parallel values are smaller than 15%. The $IC_{50}$ value is read off for the compounds indicated from dose-response graphs. The comparison compound A tested was 4-amino-2-(4,4-dimethyl-2-oxo-imidazolidin-1-yl) pyrimidine-5-(N-ethyl-N-3-trifluoromethylphenyl) carboxamide)hydrochloride, which corresponds to the compound from Example 2 of EP 0 557 879.

TABLE II

| | MTT ASSAY $IC_{50}$[mg/ml] | | |
|---|---|---|---|
| Example | HeLa | HT 29 | A 549 |
| Comparison compound A | 9.6 | 13 | 12.4 |
| 2 | >100 | >100 | >100 |
| 4 | 36 | 31 | n.d. |
| 14 | >100 | >100 | n.d. |
| 15 | >100 | >100 | n.d. |

The data from Table II demonstrate that the antiproliferative properties, and thus the cytotoxicity of the compounds of the formula I according to the invention, are greatly reduced relative to those of the comparison compound A.

The following examples serve to illustrate the invention in greater detail without restricting same to products and embodiments described in the examples.

EXAMPLE 1

Illustration of Process A

This example illustrates a method of using Process A to make a representative embodied compound, 4-Amino-2-(4, 4-dimethylimidazolidin-2-on-1-yl)-5-[N-methyl-N-(2-trifluoromethoxy)phenyl]pyrimidinecarboxamide hydrochloride.

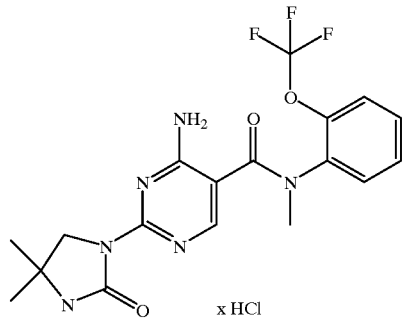

Stage 1

First, 4.2 g (16.6 mmol) of 4-amino-2-(4,4-dimethylimidazolidin-2-on-1-yl)-5-carboxylic acid are suspended in 40 ml of dry DME. Next, 5 ml (70 mmol) of thionyl chloride are added dropwise at RT, and the mixture is then refluxed for 5 h. To remove excess thionyl chloride, 35 ml of DME are distilled off. 20 ml of DME are added again, and this is distilled off. The latter procedure is repeated 3 times.

The residue is taken up with 20 ml of DME and a mixture of 3.8 g (20 mmol) of N-methyl-2-(trifluoromethoxy)aniline and 2.8 ml (20 mmol) of triethylamine is added at 40° C. The mixture is refluxed for 1.5 h and allowed to cool. After addition of 45 ml of water, the DME is removed on a rotary evaporator and the precipitate appearing during the course of this is filtered off. After purification by column chromatography on silica gel using methylene chloride/methanol (20:1), 2.4 g of 4-amino-2-(4,4-dimethylimidazolidin-2-on-1-yl)-5-[N-methyl-N-(2-trifluoromethoxy)phenyl] pyrimidinecarboxamide corresponding to 34.4% of theory are obtained.

MS: m/e 425.3 (M$^+$+1); 200 MHz $^1$H-NMR (DMSO-d$_6$, ppm): 1.30 (s, 6 H), 3.65 (s, 2 H), 7.40–7.60 (m, 3 H), 7.65–7.80 (m, 2 H), 8.40 (brs, 1 H), 8.60 (s, 1 H), 9.20 (brs, 1 H).

Stage 2

First, 2.4 g of the anilide described in Stage 1 are dissolved in 30 ml of acetone. Next, 3 ml of an ether/HCl solution (about 150 g of Hcl/l) are added dropwise with stirring in an ice bath. The mixture is stirred in the cold for 2 h and allowed to stand at RT for 3 h.

The crystal suspension thus obtained is treated with 30 ml of ether and cooled, and the hydrochloride thus obtained is filtered off with suction. Yield is 2.23 g, corresponding to 85% of theory.

M.p.: 220° C.; 200 MHz $^1$H-NMR (DMSO, ppm): 1.25 (s, 6 H), 3.60 (s, 2 H), 7.40–7.60 (m, 3 H), 7.65–7.80 (m, 2 H), 8.50 (brs, 1 H), 8.63 (brs, 1 H), 9.20 (brs, 1 H).

EXAMPLE 2

Illustration of Process B

This example demonstrates the synthesis of a representative embodied compound, 4-Amino-2-(4,4-dimethylimidazolidin-2-on-1-yl)-5-(3-trifluoromethoxyphenylpyrimidine)carboxamide, using the methods of Process B, described above.

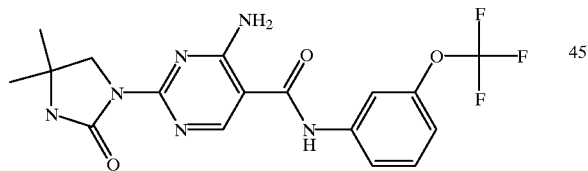

Stage 1

First, 2.0 g (11.3 mmol) of 3-trifluoromethoxyaniline are dissolved in 7 ml of dry acetonitrile with addition of 2.35 ml (17 mmol) of triethylamine. The mixture is cooled to 0° C., and 0.96 g (11.3 mmol) of cyanoacetic acid is added in portions. After 5 min at −10° C., a solution of 0.5 ml (5.65 mmol) of phosphorus trichloride in 1.7 ml of acetonitrile is added dropwise. The mixture is stirred at room temperature for 4.5 h, water is added and it is extracted with ethyl acetate. Washing of the combined organic phases with saturated NaCl solution is followed by drying over magnesium sulfate and concentration. Yield=2.8 g (=100%) of cyanoacetic acid (3-trifluoromethoxy)anilide.

M.p.: 115–117° C., MS: m/e 245 (M$^+$+1); 270 MHz $^1$H-NMR (CDCl$_3$, ppm): 3.60 (s, 2 H), 7.0–7.1 (brs, 1 H), 7.40 (m, 2 H), 7.55 (brs, 1 H), 7.85 (brs,1 H).

Stage 2

First, 2.8 g (11.3 mmol) of cyanoacetic acid (3-trifluoromethoxy)anilide are stirred at room temperature for 2 h with 8.3 ml of N,N-dimethylformamide dimethyl acetal (62 mmol). After standing overnight, purification by column chromatography using ethyl acetate/n-heptane 1:1 as eluent is carried out. Isolation of 2.8 g of 2cyano-3-N,N-dimethylaminoacrylic acid (3-trifluoromethoxyphenyl) amide (=100%).

M.p.: 128° C.; MS: m/e 300.2 (M$^+$+1); 270 MHz $^1$H-NMR (CDCl$_3$, ppm): 3.25 (s, 3 H), 3.40 (s, 3 H), 6.95 (m, 1 H), 7.35 (m, 2 H), 7.70 (m, 2 H), 7.90 (s, 1 H).

Stage 3

First, 2.7 g (9.0 mmol) of 2-cyano-3-N,N-dimethylaminoacrylic acid (3-trifluoromethoxyphenyl) amide and 1.5 g (9.9 mmol) of 1-amidino-4,4-dimethyl-2-oxoimidazolidine are refluxed for 6 hours in 100 ml of dry ethanol. The mixture is allowed to cool and is concentrated to dryness, and the residue is taken up with a little ethyl acetate. Filtering off, washing with a little cold ethyl acetate and drying in vacuo at 45° C. yield 2.0 g of 4-amino-2-(4,4-dimethylimidazolidin-2-on-1-yl)-5-[(3-trifluoromethoxy) phenyl]-pyrimidinecarboxamide. This corresponds to a yield of 54%.

M.p.: 295–297° C. (dec.); MS: m/e 411.2 (M$^+$+1); 200 MHz $^1$H-NMR (DMSO-d$_6$, ppm): 1.30 (s, 6 H), 3.70 (s, 2 H), 7.10 (m, 1 H), 7.4 (s, 1 H), 7.45 (dd, 1 H), 7.65 (brs, 3 H), 7.8 (m, 1 H), 8.7 (s, 1 H), 10.3 (s, 1 H).

EXAMPLE 3 Preparation of 4-Amino-2-(4,4-dimethyl-2-oxo-1-imidazolidin-2-on-1-yl)-5-[N-ethyl-N-(3-trifluoromethoxy)phenyl] pyrimidinecarboxamide hydrochloride

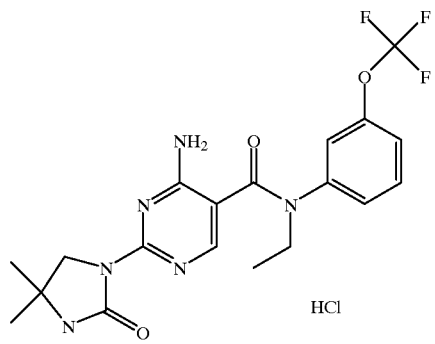

The compound was prepared analogously to Example 1.

Yield: 47%. M.p.:170° C. (dec.); MS: m/e 439.2 (M$^+$+1); 200 MHz $^1$H-NMR (DMSO-d$_6$, ppm): 1.10 (t, 3 H), 1.30 (s, 6 H), 3.60 (s, 2 H), 3.80 (q, 2 H), 7.30–7.60 (m, 4 H), 7.90 (s, 1 H), 8.55 (brs, 1 H), 8.60 (s, 1 H), 9.10 (s, 1 H).

EXAMPLE 4

Preparation of 4-Amino-2-(4,4-dimethylimidazolidin-2-on-1-yl)-5-[N-(2,2,2-trifluoroethyl)-N-(3-trifluoromethoxyphenyl)]-pyrimidinecarboxamide

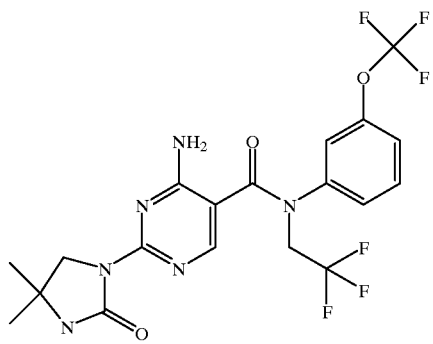

The compound was prepared analogously to Example 1.

Yield: 1%. M.p.: 115° C. MS: m/e 493.1 (M$^+$+1); 200 MHz $^1$H-NMR (DMSO, ppm): 1.20 (s, 6 H), 3.55 (s, 2 H), 4.70 (t, 2 H), 7.00 (brs, 2 H), 7.20–7.40 (m, 4 H), 7.40–7.50 (m, 1H), 7.80 (s, 1H).

EXAMPLE 5

Preparation of 4-Amino-2-(4,4-dimethylimidazolidin-2-on-1 -yl)-5-[N-(2,2,3,3,3-pentafluoropropyl)-N-(3-trifluoromethoxy)phenyl]-pyrimidinecarboxamide hydrochloride

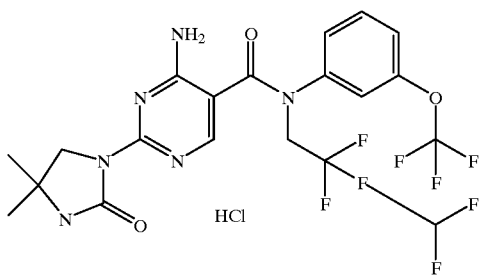

The compound was prepared analogously to Example 1.

Yield: 11%. M.p.:287° C. MS: m/e 543.1 (M$^+$+1); 200 MHz $^1$H-NMR (DMSO-d$_6$, ppm): 1.25 (s, 6 H), 3.60 (s, 2 H), 4.80 (t, 2 H), 7.35 (m, 1 H), 7.50–7.60 (m, 3 H), 8.00 (s, 1 H), 8.50–9.20 (brs, 2 H), 8.60 (s, 1 H).

EXAMPLE 6

Preparation of 4-Amino-2-(4,4-dimethylimidazolidin-2-on-1-yl)-5-[N-(3-(2,2,3,3-tetrafluoroethoxy)phenyl)]pyrimidinecarboxamide hydrochloride

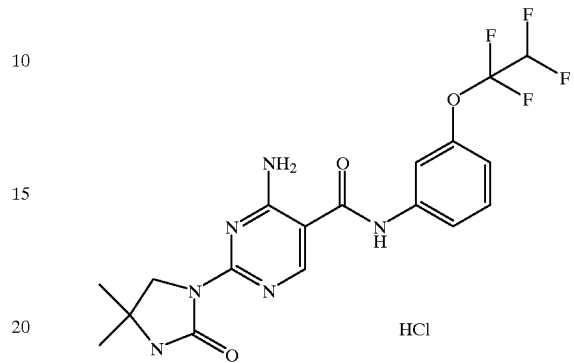

The compound was prepared analogously to Example 1.

Yield: 68%. M.p.:>300° C. MS: m/e 443.2 (M$^+$+1); 270 MHz $^1$H-NMR (DMSO-d$_6$, ppm): 1.35 (s, 6 H), 3.75 (s, 2 H), 6.85 (t, 1 H), 7.05 (m, 1 H), 7.45 (dd, 1 H), 7.70 (dd, 1 H), 7.85 (m, 1 H), 8.70 (m, 2 H), 8.80 (brs, 1 H), 9.35 (brs, 1 H), 11.40 (s, 1 H).

EXAMPLE 7

Preparation of 4-Amino-2-(4,4-dimethylimidazolidin-2-on-1 -yl)-5-[N-methyl-N-(3-(2,2,3,3-tetrafluoroethoxy)phenyl)]-pyrimidinecarboxamide hydrochloride

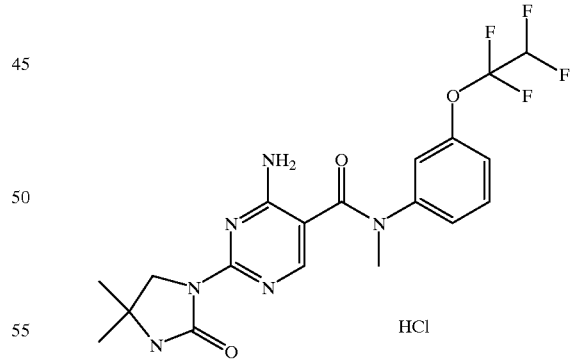

The compound was prepared analogously to Example 1.

Yield: 35%. M.p.: 240° C. (dec.); MS: m/e 457.2 (M$^+$+1); 200 MHz $^1$H-NMR (DMSO-d$_6$, ppm): 1.30 (s, 6 H), 3.40 (s, 3 H), 3.60 (s, 2 H), 6.80 (t, 1 H), 7.20 (dd, 1 H), 7.35–7.50 (m, 3 H), 7.90 (s, 1 H), 8.50 (brs, 1 H), 8.65 (s, 1 H), 9.05 (brs, 1 H).

EXAMPLE 8

Preparation of 4-Amino-2-(4,4-dimethylimidazolidin-2-on-1-yl)-5-[N-methyl-N-(4-trifluoromethoxyphenyl)]pyrimidinecarboxamide hydrochloride

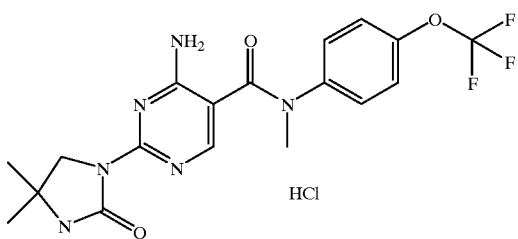

The compound was prepared analogously to Example 1.

Yield: 76%. M.p.: 283° C. MS: m/e 425.3 (M$^+$+1); 200 MHz $^1$H-NMR (DMSO-d$_6$, ppm): 1.30 (s, 6 H), 3.30 (s, 3 H), 3.60 (s, 2 H), 7.40 (d, 2 H), 7.50 (d, 2 H), 7.85 (s, 1 H), 8.55 (brs, 1 5 1 H), 8.60 (s, 1 H), 9.05 (brs, 1 H).

EXAMPLE 9

Preparation of 4-Amino-2-(4,4-dimethyl-2-imidazolidin-2-on-1-yl)-5-[N-(2-trifluoromethoxyphenyl)]pyrimidinecarboxamide- hydrochloride

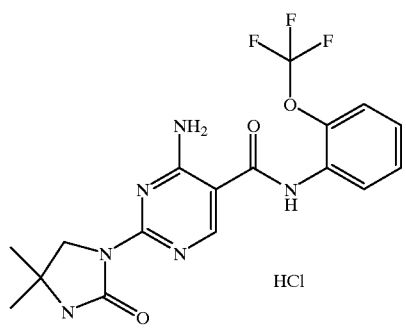

The compound was prepared analogously to Example 1.

Yield: 33%. M.p.: 295° C. MS: m/e 411.3 (M$^+$+1); 270 MHz $^1$H-NMR (DMSO-d$_6$, ppm): 1.35 (s, 6 H), 3.75 (s, 2 H), 7.35–7.50 (m, 3 H), 7.65 (m, 1 H), 8.65 (s,1 H), 8.70 (s, 1 H), 8.75–9.40 (brs, 2 H), 10.90 (s, 1 H).

EXAMPLE 10

Preparation of 4-Amino-2-(4,4-dimethylimidazolidin-2-on-1-yl)-5[N-(4-trifluoromethoxyphenyl)]pyrimidinecarboxamide hydrochloride

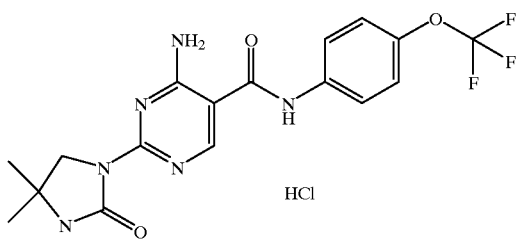

The compound was prepared analogously to Example 1.
Yield: 18%. M.p.:>300° C. MS: m/e 411.2 (M$^+$+1); 200 MHz $^1$H-NMR (DMSO-d$_6$, ppm): 1.35 (s, 6 H), 3.65 (s, 2 H), 7.40 (d, 2 H), 7.85 (d, 2 H), 8.65 (d, 2 H), 8.80 (brs, 1 H), 9.30 (brs, 1 H), 11.15 (s, 1 H).

EXAMPLE 11

Preparation of 4-Amino-2-(4,4-dimethylimidazolidin-2-on-1-yl)-5-[N-3-(difluoromethylthio)phenyl]pyrimidinecarboxamide- hydrochloride

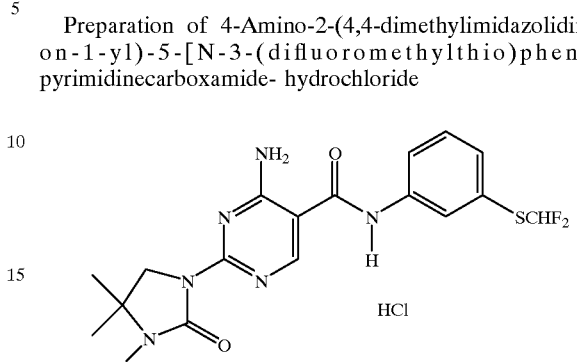

The compound was prepared analogously to Example 1.

Yield: 42%. M.p.: 294° C. (dec.); MS: m/e 409 (M$^+$+1); 200 MHz $^1$H-NMR (DMSO, ppm): 1.35 (s, 6 H), 3,78 (s, 2 H), 7.30–7.55 (m, 3 H), 7.33 (t, 1 H), 7.84 (d, 1 H), 8.05 (s, 1 H), 8.68 (s, 2 H), 8.85 (brs, 1 H), 9.32 (brs, 1 H), 11.20 (s. 1 H).

EXAMPLE 12

Preparation of 4-Amino-2-(4,4-dimethylimidazolidin-2-on-1-yl)-5-[N-methyl-(N-3-trifluoromethoxyphenyl)]pyrimidinecarboxamide

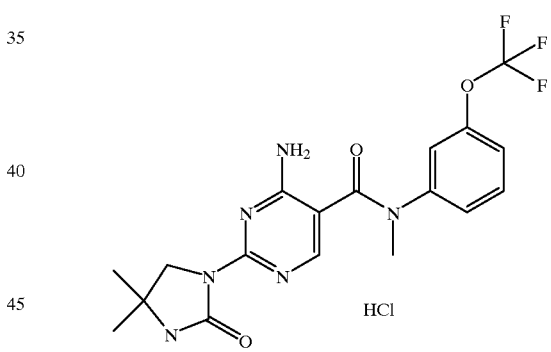

First, 484 mg (3.1 mmol) of 1-amidino-4,4-dimethylimidazolidin-2-one are suspended in 3 ml of dry DME and a solution of 800 mg of 2-cyano-3-ethoxyacrylic acid (3-trifluoromethoxyphenyl)amide in 7 ml of the same solvent are added dropwise at 0° C. The mixture is stirred at RT for 3 h and treated with 3 ml of glacial acetic acid. The clear solution is allowed to stand overnight and is heated for a further 2 h at 70° C. to complete the reaction. It is neutralized with sodium hydrogen carbonate solution and extracted with ethyl acetate, and the organic phase is washed with sat. NaCl solution and dried over magnesium sulfate.

After purification by column chromatography on silica gel (ethyl acetate/methanol 20:1), 300 mg of a white solid are obtained (=27.2%).

M.p.: 185° C. MS: m/e 425.2 (M$^+$+1); 200 MHz $^1$H-NMR (DMSO-d$_6$, ppm): 1.20 (s, 6 H), 3.35 (s, 3 H), 3.55 (s, 2 H), 6.95 (brs, 2 H), 7.20-7.40 (m, 4 H), 7.45 (m, 1 H), 7.75 (s, 1 H).

EXAMPLE 13

Preparation of 4-Amino-2-(4,4-dimethylimidazolidin-2-on-1-yl)-5[N-(3-difluoromethoxyphenyl)]pyrimidinecarboxamide-hydrochloride

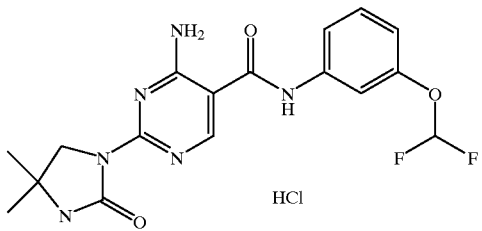

The compound was prepared analogously to Example 1.
Yield: 77%. M.p.: 306° C.; MS: m/e 393 (M$^+$+1); 200 MHz $^1$H-NMR (DMSO-d$_6$, ppm): 1.35 (s, 6 H), 3.75 (s, 2 H), 6.95 (dd, 1 H), 7.20 (t, 1 H), 7.40 (t, 1 H), 7.55–7.70 (m, 2 H), 8.70 (s, 1 H), 8.75 (s, 1 H), 8.85 (brs, 1 H), 9.35 (brs, 1 H), 11.25 (s, 1 H).

EXAMPLE 14

Preparation of 4-Amino-2-(4,4-dimethylimidazolidin-2-on-1 -yl)-5-[N-(2,2-difluorobenzo-1,3-dioxol-5-yl)]pyrimidinecarboxamide-hydrochloride

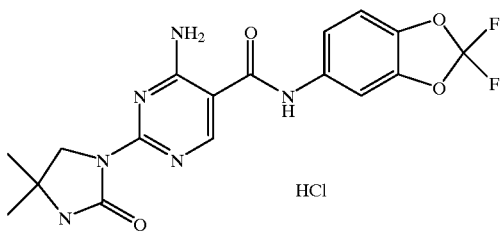

The compound was prepared analogously to Example 1.
Yield: 81%. M.p.: 316° C.; MS: m/e 407 (M$^+$+1); 200 MHz $^1$H-NMR (DMSO-d$_6$, ppm): 1.35 (s, 6 H), 3.75 (s, 2 H), 7.45 (d, 1 H), 7.55 (dd, 1 H), 7.90 (d, 1 H), 8.75 (s, 1 H), 8.85 (brs, 1 H), 9.35 (brs, 1 H), 11.40 (s, 1 H).

EXAMPLE 15

Preparation of 4-Amino-2-(4,4-dimethylimidazolidin-2-on-1 -yi)-5-[N-(2,2, 3, 3-tetrafluorobenzo-1,4-dioxan-6-yl)]-pyrimidinecarboxamide hydrochloride

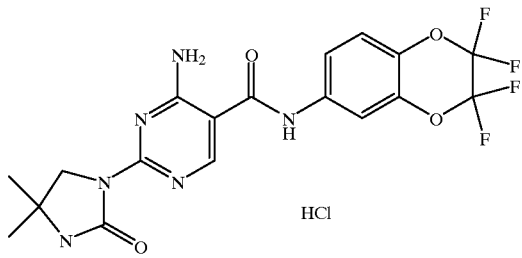

The compound was prepared analogously to Example 1.
Yield: 96%. M.p.: 315° C.; MS: m/e 557 (M$^+$+1); 200 MHz $^1$H-NMR (DMSO-d$_6$, ppm): 1.35 (s, 6 H), 3.75 (s, 2 H), 7.50 (d, 1 H), 7.65 (dd, 1 H), 7.90 (d, 1 H), 8.65 (s, 1 H), 8.70 (s, 1 H), 8.80 (brs, 1 H), 9.25 (brs, 1 H), 11.40 (s, 1 H).

EXAMPLE 16

Preparation of 4-Amino-2-(4,4-dimethylimidazolidin-2-on-1-yl)-5-[N-(3-chloro-4-trifluoromethoxyphenyl)]pyrimidinecarboxamide-hydrochloride

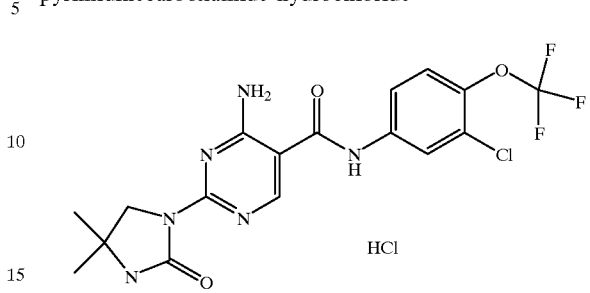

The compound was prepared analogously to Example 1.
Yield: 79%. M.p.: 321° C.; MS: m/e 445, 447 (M$^+$+1); 200 MHz $^1$H-NMR (DMSO-d$_6$, ppm): 1.35 (s, 6 H), 3.75 (s, 2 H), 7.60 (d, 1 H), 7.80 (dd, 1 H), 8.15 (d, 1 H), 8.65 (s, 1 H), 8.70 (s, 1 H), 8.80 (brs, 1 H), 9.35 (brs, 1 H), 11.45 (s, 1 H).

EXAMPLE 17

Preparation of 4-Amino-2-(4,4-dimethylimidazolidin-2-on-1-yl)-5-[N-(3-bromo-4-trifluoromethoxyphenyl)]pyrimidinecarboxamide-hydrochloride

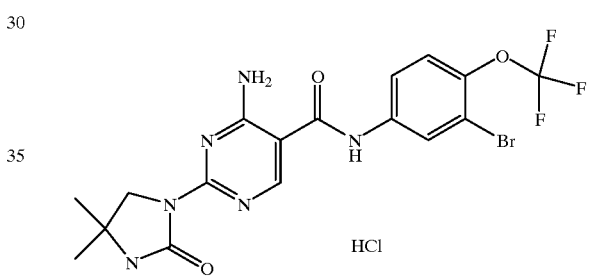

The compound was prepared analogously to Example 1.
Yield: 86%. M.p.: 322° C.; MS: m/e 489, 491 (M$^+$+1); 200 MHz $^1$H-NMR (DMSO-d$_6$, ppm): 1.35 (s, 6 H), 3.75 (s, 2 H), 7.55 (dd, 1 H), 7.85 (dd, 1 H), 8.30 (d, 1 H), 8.80 (brs, 1 H), 9.30 (brs, 1 H), 11.40 (s, 1 H).

EXAMPLE 18

Preparation of 4-Amino-2-(4,4-dimethylimidazolidin-2-on-1-yl)-5-[N-3-(2,2,2-trifluoroethoxy)phenyl]pyrimidinecarboxamide-hydrochloride

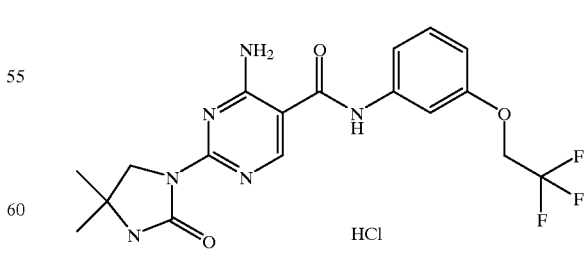

The compound was prepared analogously to Example 1.
Yield: 73%. M.p.: 313° C.; MS: m/e 425 (M$^+$+1); 200 MHz $^1$H-NMR (DMSO-d$_6$, ppm): 1.35 (s, 6 H), 3.75 (s, 2 H), 4.75 (q, 2 H), 6.70 (d, 1 H), 7.25–7.45 (m, 2 H), 7.55 (s, 1 H), 8.65 (s, 1 H), 8.70(s, 1 H), 8.85 (brs, 1 H), 9.35 (brs, 1 H), 11.15 (s, 1 H).

EXAMPLE 19

Preparation of 4-Amino-2-(4,4-dimethylimidazolidin-2-on-1-yl)-5-[N4-(2,2,2-trifluoroethoxy)phenyl]pyrimidinecarboxamide-hydrochloride

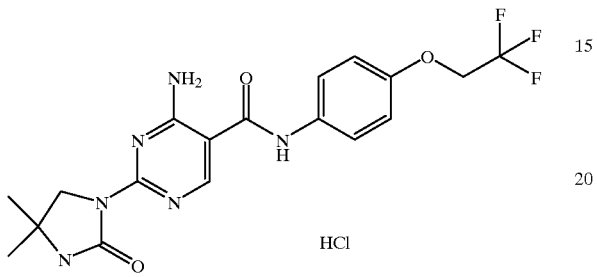

The compound was prepared analogously to Example 1.

Yield: 61%. M.p.: 324° C.; MS: m/e 425 (M$^+$+1); 200 MHz $^1$H-NMR (DMSO-d$_6$, ppm): 1.35 (s, 6 H), 3.75 (s, 2 H), 4.75 (q, 2 H), 7.10 und 7.70 (AA'BB'-System, 4 H), 8.65 (s, 1 H), 8.70 (s, 1 H), 8.80 (brs, 1 H), 9.30 (brs, 1 H), 11.00 (s, 1 H).

EXAMPLE 20

Preparation of 4-Amino-2-(4,4-dimethylimidazolidin-2-on-1-yl)-5-[N-(3-pentafluoroethoxy)-phenyl]pyrimidinecarboxamide

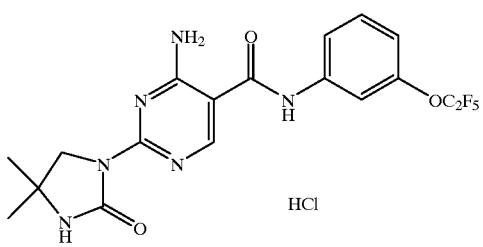

The compound was prepared analogously to Example 1.

Yield: 40%. M.p.: 294° C. (dec.); MS: m/e 461 (M$^+$+1); 200 MHz $^1$H-NMR (DMSO-d$_6$, ppm): 1.35 (s, 6 H), 3.75 (s, 2 H), 7.13 (d, IH), 7.50 (t, 1 H), 7.74 (d, 1 H), 7.90 (s, 1 H), 8.66 (s, 2 H), 8.87 (brs, 1 H), 9.32 (brs, 1 H), 11.30 (s, 1 H).

EXAMPLE 21

Preparation of 4-Amino-2-(4,4-dimethylimidazolidin-2-on-1-yl)-N-(6-fluoro-3-trifluoromethoxyphenyl)pyrimidinecarboxamide

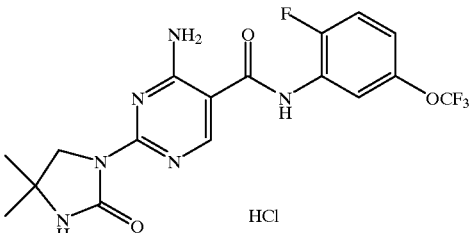

The compound was prepared analogously to Example 1.

Yield: 17%; M.p.: 265° C.; MS: m/e 429.2 (M$^+$+1); 200 MH$_2$ $^1$H-NMR (DMSO-d$_6$, ppm): 1.25 (s, 6 H), 3.75 (s, 2 H), 7,30 (m, 1 H), 7.40–7.50 (m, 2 H), 7.60–7.75 (m, 3 H), 8.70 (s, 1 H), 10.15 (s, 1 H).

EXAMPLE 22

Preparation of 4-Amino-2-(4,4-dimethylimidazolidin-2-on-1-yl)-5-[N-(3-trifluorothiomethyl-phenyl)]pyrimidinecarboxamide-hydrochloride

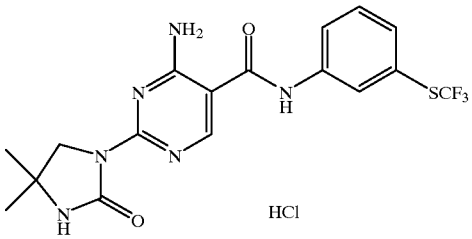

The compound was prepared analogously to Example 1.

Yield: 37%, M.p.:>300° C. MS: m/e 427.2 (M$^+$+1); 200 MHz $^1$H-NMR (DMSO, ppm): 1.30 (s, 6 H), 3.75 (s, 2 H), 7.40–7.60 (m, 2 H), 7.90 (m, 1 H), 8.20 (s, 1 H), 8.70 (m, 2 H), 8.80 (brs, 1 H), 9.30 (brs, 1 H), 11.30 (s, 1 H).

Abbreviations

The abbreviations used in the description have the following meanings:

| | |
|---|---|
| DME | Dimethoxyethane |
| NEt$_3$ | Triethylamine |
| LDL | low-density lipoprotein |
| h | hour |
| NMP | N-Methylpyrrolidone |
| DMF | Dimethylformamide |

The entire content of German Patent Application No. 196 25 089.7, filed Jun. 24, 1996, is hereby incorporated by reference.

The present invention has been described with reference to certain preferred embodiments thereof. It is to be understood that the invention is not to be limited in any way be these exemplary embodiments but rather is to be defined by the scope of the appended claims.

We claim:
1. A 4-amino-2-ureidopyrimidine-5-carboxamide compound of formula I,

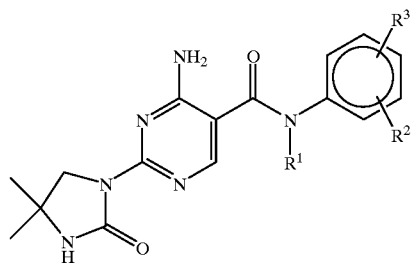

in which
R$^1$ is hydrogen or a (C$_1$–C$_8$)-alkyl, in which one or more or all hydrogens can be replaced by fluorine,
R$^2$ is selected from the group consisting of fluorine, chlorine, bromine, hydrogen, -O-(C$_1$–C$_8$)-alkyl, and -S-(C$_1$–C$_8$)-alkyl, where the alkyl radicals have one or more or all hydrogens replaced by fluorine,
R$^3$ is -O-(C$_1$–C$_8$)-alkyl or -S-(C$_1$–C$_8$)-alkyl, where the alkyl radicals have one or more or all hydrogens replaced by fluorine, or
R$^2$ and R$^3$ together can form a radical of the formula -O-(C$_1$–C$_5$)-alkylene-O-, where the alkylene portion has one or more or all hydrogens replaced by fluorine, or a physiologically tolerable acid addition salt thereof.

2. A compound according to claim 1, wherein:
R$^1$ is (C$_1$–C$_4$)-alkyl, in which one or more or all hydrogens can be replaced by fluorine,
R$^2$ is selected from the group consisting of fluorine, chlorine, bromine, hydrogen, -O-(C$_1$–C$_4$)-alkyl, and -S-(C$_1$–C$_4$)-alkyl, where the alkyl radicals have one or more or all hydrogens replaced by fluorine,
R$^3$ is -O-(C$_1$–C$_4$)-alkyl or -S-(C$_1$–C$_4$)-alkyl, where the alkyl radicals have one or more or all hydrogens replaced by fluorine, or
R$^2$ and R$^3$ together can form a radical of the formula -O-(C$_1$–C$_5$)-alkylene-O-, where the alkylene portion has one or more or all hydrogens replaced by fluorine, or a physiologically tolerable acid addition salt thereof.

3. A compound according to claim 1, wherein:
R$^1$ is (C$_1$–C$_4$)-alkyl, in which one or more or all hydrogens can be replaced by fluorine,
R$^2$ is hydrogen or bromine,
R$^3$ is -OCF$_3$,
or a physiologically tolerable acid addition salt thereof.

4. A compound according to claim 1, wherein the compound is selected from the group consisting of 4-Amino-2-(4,4-dimethylimidazolidin-2-on-1-yl)-5-[N-methyl-N-(2-trifluoromethoxy)phenyl]pyrimidinecarboxamide hydrochloride, 4-Amino-2-(4,4dimethylimidazolidin-2-on-1-yl)-5-(N-3-trifluoromethoxyphenylpyrimidine) carboxamide, 4-Amino-2-(4,4-dimethyl-2-oxo-1-imidazolidin-2-on-1-yl)-5-[N-ethyl-N-(3-trifluoromethoxy) phenyl]pyrimidinecarboxamide hydrochloride, 4-Amino-2-(4,4dimethylimidazolidin-2-on-1-yl)-5-[N-(2,2,2-trifluoroethyl)-N-(3-trifluoromethoxyphenyl)] pyrimidinecarboxamide, 4-Amino-2-(4,4-dimethylimidazolidin2-on-1-yl)-5-[N-(2,2,3,3,3-pentafluoropropyl)-N-(3-trifluoromethoxy)phenyl] pyrimidinecarboxamide hydrochloride, 4-Amino-2-(4,4-dimethylimidazolidin-2-on-1-yl)-5-[N-(3-(2,2,3,3-tetrafluoroethoxy)phenyl)]pyrimidinecarboxamide hydrochloride, 4-Amino-2-(4,4-dimethylimidazolidin-2-on-1-yl)-5-[N-methyl-N-(3-(2,2,3,3-tetrafluoroethoxy)phenyl)] pyrimidinecarboxamide hydrochloride, 4-Amino-2-(4,4-dimethylimidazolidin-2-on-1-yl)-5-[N-methyl-N-(4-trifluoromethoxyphenyl)]pyrimidinecarboxamide hydrochloride, 4-Amino-2-(4,4-dimethylimidazolidin-2-on-1-yl)-5-[N-(2-trifluoromethoxyphenyl)] pyrimidinecarboxamide hydrochloride, 4-Amino-2-(4,4-dimethylimidazolidin-2-on-1-yl)-5-[N-(4-trifluoromethoxyphenyl)]pyrimidinecarboxamide hydrochloride, 4-Amino-2-(4,4-dimethylimidazolidin-2on-1-yl)-5-[N-3-(difluoromethylthio)phenyl] pyrimidinecarboxamide hydrochloride, 4Amino-2-(4,4-dimethylimidazolidin-2-on-1-yl)-5-[N-methyl-(3-trifluoromethoxyphenyl)]pyrimidinecarboxamide, 4-Amino-2-(4,4-dimethylimidazolidin-2-on-1-yl)5-[N-(3-difluoromethoxyphenyl)]pyrimidinecarboxamide hydrochloride, 4-Amino-2-(4,4-dimethylimidazolidin-2-on-1-yl)-5-[N-(2,2-difluorobenzo-1,3-dioxol-5-yl)] pyrimidinecarboxamide hydrochloride, 4-Amino-2-(4,4-dimethylimidazolidin-2-on-1yl)-5-[N-(2,2,3,3-tetrafluorobenzo-1,4-dioxan-6-yl)]pyrimidinecarboxamide hydrochloride, 4-Amino-2-(4,4-dimethylimidazolidin-2-on-1-yl)-5-[N-(3-chloro-4-trifluoromethoxyphenyl)] pyrimidinecarboxamide hydrochloride, 4-Amino-2-(4,4-dimethylimidazolidin-2-on-1-yl)-5-[N-(3-bromo-4-trifluoromethoxyphenyl)]pyrimidinecarboxamide hydrochloride, 4-Amino-2-(4,4-dimethylimidazolidin-2-on-1-yl)-5-[N-3-(2,2,2-trifluoroethoxy)phenyl] pyrimidinecarboxamide hydrochloride, 4-Amino-2-(4,4-dimethylimidazolidin-2-on-1-yl)-5-[N-4-(2,2,2-trifluoroethoxy)phenyl]pyrimidinecarboxamide hydrochloride, 4-Amino-2-(4,4-dimethylimidazolidin-2-on-1-yl)-5-[N-(3-pentafluoroethoxy)-phenyl] pyrimidinecarboxamide, 4-Amino-2-(4,4-dimethylimidazolidin-2-on-1-yl)-N-(6fluoro-3-trifluoromethoxyphenyl)pyrimidinecarboxamide, 4-Amino-2-(4,4-dimethylimidazolidin-2-on-1-yl)-5-[N-(3-trifluorothiomethylphenyl)]pyrimidinecarboxamide hydrochloride and physiologically tolerable acid addition salts thereof.

5. A process for preparing a compound of claim 1 comprising:

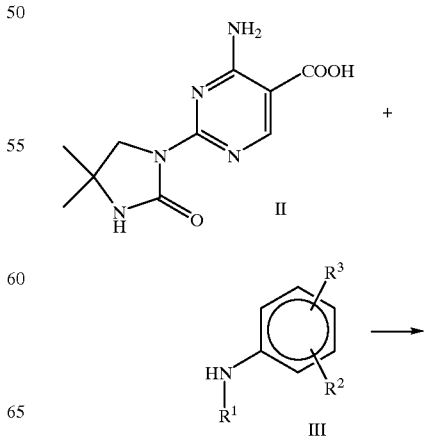

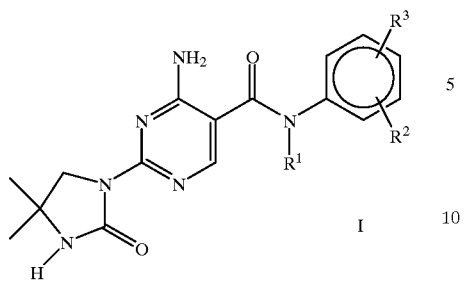

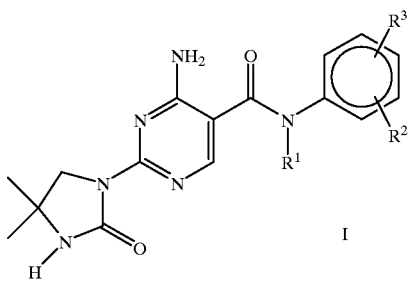

converting a compound of formula II into its corresponding acid chloride and reacting said acid chloride with a compound of formula III, in which $R^1$, $R^2$ and $R^3$ are defined as in claim 1, at a temperature from 0° C. to 200° C. in a suitable solvent, optionally with addition of an auxiliary base, to give a compound of formula I, and optionally converting said compound of formula I into a physiologically tolerable salt or converting a salt obtained into a physiologically tolerable salt.

6. A process for preparing the compounds of claim 1 comprising the following reaction scheme

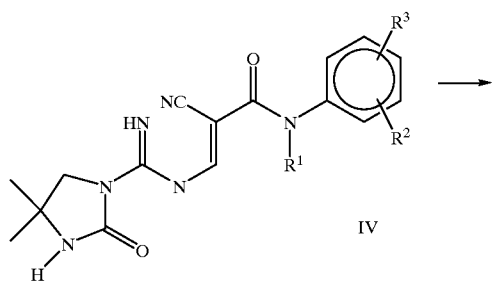

cyclizing a compound of formula IV, in which $R^1$, $R^2$ and $R^3$ are defined as in claim 1, to a compound of formula I.

7. A pharmaceutical preparation comprising one or more compounds of claim 1 and a suitable carrier..

8. A pharmaceutical preparation according to claim 7, wherein said one or more compounds is present in a concentration of approximately 0.1 to 99 percent by weight.

9. A pharmaceutical preparation according to claim 8, wherein said one or more compounds is present in a concentration of approximately 0.5 to 70 percent by weight.

10. A process for producing a pharmaceutical preparation according to claim 7, comprising admixing said one or more compounds with a pharmaceutically suitable excipient.

11. A method of treating disorders of lipid metabolism, comprising administering to a patient in need of such treatment, a therapeutically effective amount of a preparation comprising at least one compound according to claim 1.

12. The method of claim 3, wherein the disorder of lipid metabolism is hyperlipidemia.

13. The method of claim 11, wherein said preparation is administered orally, parenterally, intraperitoneally, rectally or by a combination thereof.

* * * * *